United States Patent [19]

Davey et al.

[11] Patent Number: 5,882,862
[45] Date of Patent: Mar. 16, 1999

[54] HUMAN RADIORESISTANCE/CELL CYCLE PROGRESSION GENE

[75] Inventors: Scott K. Davey, Ontario, Canada; Howard B. Lieberman, Tenafly; Kevin M. Hopkins, Fort Lee, both of N.J.

[73] Assignees: The Trustees of Columbia University in the City of New York, New York, N.Y.; The Ontario Cancer Treatment and Research Foundation, Ontario, Canada

[21] Appl. No.: 644,034

[22] Filed: May 9, 1996

[51] Int. Cl.$^6$ .............................. C12Q 1/68; C07H 21/04
[52] U.S. Cl. ................................. 435/6; 536/23.1
[58] Field of Search ................... 536/23.1, 23.2, 536/24.3, 24.31; 435/69.1, 320.1, 272.3, 6

[56] References Cited

PUBLICATIONS al–Khodairy, F. and A.M. Carr (1992) "DNA repair mutants defining G$_2$ checkpoint pathways in *Schizosaccharomyces pombe*." *Embo J* 11: 1343–1350.

Barker, H.M., et al. (1990) "Localization of the gene encoding a type 1 protein phosphatase catalytic subunit to human chromosome band 11q13." *Genomics* 7: 159–166.

Duyao, M.P., et al. (1995) "Inactivation of the mouse Huntington's disease gene homolog Hdh." *Science* 269: 407–410.

Enoch, T., et al. (1992) "Fission yeast gene involved in coupling mitosis to completion of DNA replication." *Genes Dev* 6: 2035–2046.

Griffin, E.F. and H. Harris (1992) "Total inhibition of involucrin synthesis by a novel two–step antisense procedure; further examination of the relationship between differentiation and malignancy in hybrid cells." *J. Cell Science* 102: 799–805.

Jesudasan, R.A., et al. (1995) "Deletion and translocation of chromosome 11q13 sequences in cervical carcinoma cell lines." *Am J Hum Genet* 56: 705–715.

Larsson, C., et al. (1988) "Multiple endocrine neoplasia type 1 gene maps to chromosome 11 and is lost in insulinoma." *Nature* 332: 85–87.

Larsson, C., et al. (1992) "Isolation and mapping of polymorphic cosmid clones used for sublocalization of the multiple endocrine neoplasia type 1 (MEN1) locus." *Hum Genet* 89: 187–193.

Larsson C., et al. (1994) "Localization and identification of the multiple endocrine neoplasia type 1 disease gene." *Endocrinol Metab Clin North Am* 23: 67–79.

Lieberman, H.B., et al. (1992) "Molecular cloning and analysis of *Schizosaccharomyces pombe* rad9, a gene involved in DNA repair and mutagenesis." *Mol Gene Genet* 232: 367–376.

Lieberman, H.B. and K.M. Hopkins (1994) "*Schizosaccharomyces malidevorans* and *Sz. octosporus* homologues of *Sz. pombe* rad9, a gene that mediates radioresistance and cell–cycle progression." *Gene* 150: 281–286.

Lieberman, H.B. (1995) "Extragenic suppressors of *Schizosaccharomyces pombe* rad9 mutations uncouple radioresistance and hydroxyurea sensitivity from cell cycle checkpoint control." *Genetics* 141: 107–117.

Okazaki, K., et al. (1990) "High–frequency transformation method and library transducing vectors for cloning mammalian cDNAs by trans–complementation of *Schizosaccharomyces pombe*." *Nucleic Acids Res* 18: 6485–6489.

Savitsky, K., et al. (1995) "A single ataxia telangiectasia gene with a product similar to PI–3 kinase." *Hum Mol Gen* 268: 1749–1753.

Soares, M.B., et al. (1994) "Construction and characterization of a normalized cDNA library." *Proc Natl Acad Sci U.S.A.* 91: 9228–9232.

Weinert, T.A. and L.H. Hartwell (1990) "Characterization of RAD9 of *Saccharomyces cerevisiae* and evidence that its function acts posttranslationally in cell cycle arrest after DNA damage." *Mol Cell Biol* 10: 6554–6564.

*Primary Examiner*—Eggerton A. Campbell
*Attorney, Agent, or Firm*—John P. White; Cooper & Dunham LLP

[57] ABSTRACT

This invention provides isolated nucleic acids which encode a wildtype and a mutant human homolog of RAD9. This invention also provides purified and mutant wildtype human homologs of RAD9. This invention also provides methods for determining whether a subject has radiosensitivity; for predicting the effect of radiation therapy or chemotherapy on a subject; for detecting whether a subject has a predisposition to cancer; for treating a subject who is radiosensitive and for preventing or treating cancer in a subject who is radiosensitive.

12 Claims, 10 Drawing Sheets

FIG. 1A

| | | |
|---|---|---|
| S. octosporus | 1 | MEFVVSNTNLRDLSRIFLNLSRIDDAVNWEINKQQLILTTLNSSRSGPGKVTLTKQFPDK |
| H. sapiens | 1 | MKCLVTGGNVKVLGKAVHSLSRIGDRLYLEPLEDGLSLRTVNSSRSAYACFLFAPLFPQQ |
| S. pombe | 1 | MEFTVSNVNLRDLARIFTNLSRIDDAVNWEINKNQIEITCLNSSRSGFSMVTLKKAFFDK |
| S. octosporus | 61 | PTFHPDTLPLTGFVSPTVRLSTQIKPILSIPRNKIFESTLLVNNNLNTNAGAAESSSKQN |
| H. sapiens | 61 | YQAATPGQDL.......LRCKILMKSFLSVFR............................SLAMLE |
| S. pombe | 61 | YIPQPDSVLLTGLMTPTIRIRTQVKPILSVFRNKIFDFIPTVVTTNSKNGYGSESASRKD |
| S. octosporus | 121 | VVVENIQMQITSGKECRVIFKFNCKHGVVKTYKIAYEQTQTLHAVFDKASCHNNWQINSK |
| H. sapiens | 92 | KTVEKCCISL.NGRSSRLVVQLHCKFGVRKTHNLSFQDCESLQAVFDPASCPHMLRAPAR |
| S. pombe | 121 | VIVENVQISISTGSECRIIFKFLCKHGVIKTYKISYEQTQTLHAVFDKSLSHNNPQINSK |
| S. octosporus | 181 | ILKDLIEHFGQKTEELTIQPVQG.RVLLTSFTEEVVHNKDVLKQPTQTTVSIDGKFEQV |
| H. sapiens | 151 | VLGEAVLPFSPALAEVTLGIGRGRRVILRSYHER...EADSTAKAMVTEMCLGEEDPQQL |
| S. pombe | 181 | ILKDLTEHFGQRTEELTIQPLQE.RVLLTSFTEEVVHNRDILKQPTQTTVSIDGKFERV |
| S. octosporus | 240 | SLNEGIIITLSLREFRAAVLLAESLGTSIASYYSVSGKPALFTNKGKFMEIEAQPILAT |
| H. sapiens | 208 | QAQEGVAITPCLKEFRGLLSFAESANLNLSIHFDAPGRPAIFTI...KDSLLDGHPVLAT |
| S. pombe | 240 | ALNEGVSVTLSLREFRAAVILAEALGSSICAYYGVPGKPILLTPAKGKNSEIEAQPILAT |

FIG. 1B

| | | |
|---|---|---|
| S. octosporus | 300 | VMGPDDFDESS.LGARWQQSGTANSSLLVPENTSAAPALENEAPSASIGWQTNGDAETSR |
| H. sapiens | 265 | LSDTDSHSQDLGSPERHQ.....PVPQLQAHSTPHPDDPANDDIDSYMIAMETTIGNEGSR |
| S. pombe | 300 | VVGSDEQEVSSMMGNRWQHSSTPASLPNSVERNNSLTAVAHNPP.GSIGWQT.DQSDSSR |
| S. octosporus | 359 | MPHSTLDIPRNEEPAAKPSRQTTDEENHPLPLEGMPDETELMAPDNDVADDAEPGPTQHE |
| H. sapiens | 321 | VLPSISLSPGPQPPKSPGPHSEEEDRAEPSTVPGTPPPKKPRSLPP....GSILAPVRSP |
| S. pombe | 358 | MFNSALD..RSDETNGIKEPSTTNDAGQSLPLDGIPNESELAAPNNDVNDDAEPGPTQAE |
| S. octosporus | 419 | QTYHGIFSQDDTET. 432 |
| H. sapiens | 377 | QGPSPVLAEDSEGEG 391 |
| S. pombe | 416 | QSYHGIFSQED.... 426 |

FIG. 5C

```
Oligonucleotide orientation    ---------->
HRAD9 cDNA sequence            CATGGTGACTGAGATGTGCCTTGGAGAGGAGGATTTCCAGCAGCTGCAGGCCCAGGAAGGGGTG
HRAD9 genomic DNA sequence                                                     GCAGCTGCAGGCCGAGGAAGGGGTG Oligonucleotide orientation    ---------->
HRAD9 cDNA sequence            GCCATCACTTTCTGCCTCAAGGAATTCCGGG.........
HRAD9 genomic DNA sequence     GCCATCACTTTCTGCCTCAAGGAATTCCGGGTGAGTTCCTCCCAGGCTCGCCGTCCTGTCC Oligonucleotide orientation                                                              ---------->
HRAD9 cDNA sequence            .........GGCTCCTGAGCT
HRAD9 genomic DNA sequence     TCCCTGCCCAGCTCAGCCCCAGCCCCGGGCCCTCACCTGCACCTCTTCTCCAGGGCTCCTGAGCT Oligonucleotide orientation                                                 <----------
HRAD9 cDNA sequence            TTGCAGAGTCAGCAAACTTGAATCTTAGCATTCATTTTGATGCTCCAGGCAGGCCCGCCATCTT
HRAD9 genomic DNA sequence     TTGCAGAGTCAGCAAACTTGAATCTTAGCATTCATTTTGATGCTCCAGGCAGG Oligonucleotide orientation    <----------
HRAD9 cDNA sequence            CACCATCAAGGACTCTTTG
HRAD9 genomic DNA sequence
```

HUMAN RADIORESISTANCE/CELL CYCLE PROGRESSION GENE

The invention disclosed herein was made with Government support under Grant Nos. CA12536, GM52493 and CA68446 from the National Institutes of Health of the U.S. Department of Health and Human Services. Accordingly, the U.S. Government has certain rights in this invention.

BACKGROUND OF THE INVENTION

Throughout this application, various publications are referenced by Arabic numerals. Full citations for these publications may be found listed at the end of the specification immediately preceding the Sequence Listing. The disclosures of these publications in their entireties are hereby incorporated by reference into this application in order to more fully describe the state of the art as known to those skilled therein.

The product of the *Schizosaccharomyces pombe* rad9 gene is required for cell cycle arrest at the G2 checkpoint in response to incompletely replicated or damaged DNA. Cell cycle checkpoints are regulatory mechanisms that prevent cell cycle progression in the presence of DNA damage or incompletely replicated DNA (1–4). In the fission yeast *S. pombe*, loss of any of the rad1, rad3, rad9, rad17, or hus1 genes abolished the G2 checkpoint delays which usually follow exposure to DNA damaging or replication blocking agents (3–5). This result suggests that these five genes regulate a single common pathway linking aberrant DNA structures to cell cycle control. Evidence for the conservation of checkpoint control pathways at the molecular level is suggested by the similarity of the gene product of the human ATM (*Ataxia telangiectasia* mutated) locus and the proteins encoded by the checkpoint genes rad3 from *S. pombe* and MEC1 from *S. cerevisiae* (6). It is likely that the ATM gene product is involved in checkpoint control in human cells, as cell lines derived from AT patients exhibit a number of defects indicative of checkpoint deficiency, including sensitivity to ionizing radiation (8), and an increased rate of spontaneous mutation (8). However, the primary defect in AT seems to be at the G1-S rather than at the G2-M checkpoint (9, 10).

SUMMARY OF THE INVENTION

This invention provides isolated nucleic acids which encode a wildtype human homolog of RAD9, as well as, mutants thereof.

This invention also provides a vector which includes the isolated nucleic acid which encodes a wildtype human homolog of RAD9 and a host vector system which includes this vector.

This invention also provides a method of producing a polypeptide which comprises growing such a host vector system under suitable conditions permitting the production of the polypeptide and recovering the polypeptide so produced. This invention also provides purified wildtype and mutant human homologs of RAD9.

This invention further provides an oligonucleotide of at least 15 nucleotides capable of specifically hybridizing with a unique sequence of nucleotides within a nucleic acid which encodes a wildtype human homolog of RAD9 without hybridizing to any nucleic acid which encodes a mutant human homolog of RAD9. This invention also provides an oligonucleotide of at least 15 nucleotides capable of specifically hybridizing with a unique sequence of nucleotides within a nucleic acid which encodes a mutant human homolog of RAD9 without hybridizing to any nucleic acid which encodes a wildtype human homolog of RAD9.

This invention also provides methods for determining whether a subject has radiosensitivity and for treating a subject who is radiosensitive.

This invention still further provides a method for predicting the effect of radiation therapy or chemotherapy on a subject.

This invention also provides a method for detecting whether a subject has a predisposition to cancer; and a method for preventing cancer in a subject who is radiosensitive. This invention also provides a method for treating a subject who has cancer.

This invention additionally provides transgenic, nonhuman mammals which express either a wildtype human homolog of RAD9 gene or a mutant human homolog of the RAD9 gene.

Finally, this invention provides a method for detecting the presence of human chromosomal region 11q13 in a sample of genomic DNA.

BRIEF DESCRIPTION OF THE FIGURES

FIGS. 1A and 1B

Comparison of amino acid sequences predicted for the rad9 gene products from *S. pombe* and *S. octosporus*, and the human homolog of rad9 gene product from *H. sapiens*.

Numbers on the left indicate the next amino acid in the protein sequence. Symbols between amino acids: line, identical amino acids; colon, similar amino acids. The amino acid sequence of the human homolog of rad9 is designated Sequence ID No.: 1; the amino acid sequence of rad9 from *S. octosporus* is designated Sequence ID No.: 2; and the amino acid sequence of rad9 from *S. pombe* is designated Sequence ID No.: 3.

1A. Comparison of amino acid sequences from amino acid 1 to 299 for *S. octosporus* (top), amino acid 1 to 264 for *H. sapiens* (middle), and amino acid 1 to 299 for *S. pombe* (bottom).

1B. Comparison of amino acid sequences from amino acid 300 to 432 for *S. octosporus* (top), amino acid 265 to 391 for *H. sapiens* (middle), and amino acid 300 to 426 for *S. pombe* (bottom).

Figure 2A:
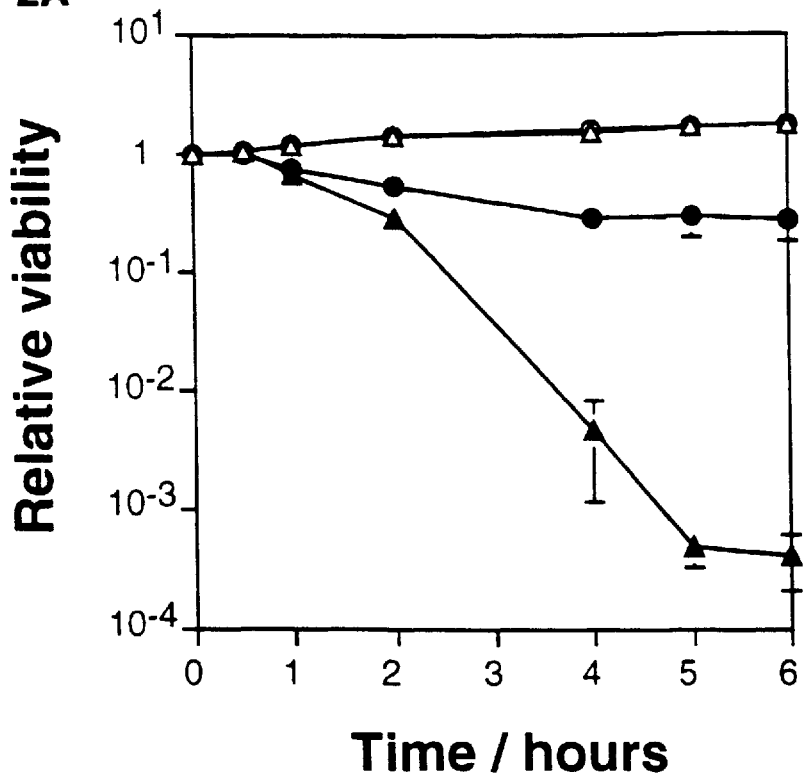
Figure 2B:
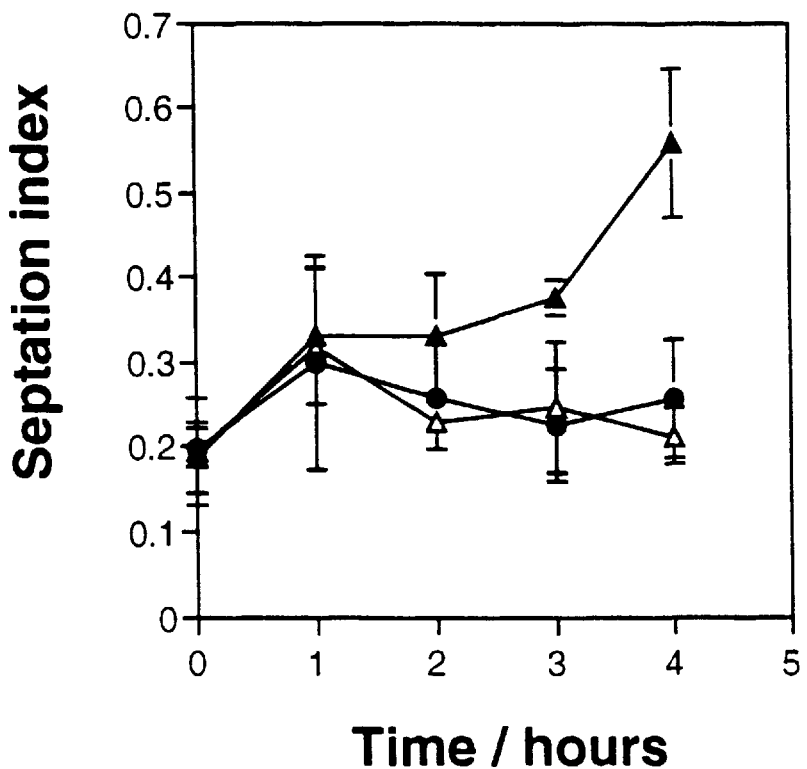

FIGS. 2A and 2B

Wildtype human homolog of RAD9 expression increases cell survival and cell cycle delay of rad9 null strains transiently exposed to hydroxyurea.

2A. *S. pombe* cells were cultured to mid-log phase, and hydroxyurea added to 10 mM. The fraction of the population surviving was determined at the indicated times after hydroxyurea addition, using a colony formation assay. Strains: rad9+(Δ), rad9+[pHRAD9-1] (○), rad9::ura4+(>), rad9::ura4+[pHRAD9-1] (●). 2B. Hydroxyurea-induced cell cycle delay was determined using an asynchronous population of *S. pombe* exposed to 12 mM hydroxyurea. At the indicated times, aliquots of the culture were taken and fixed with ethanol. Samples were washed once, stained with calcofluor, and examined for septation by fluorescence microscopy. Strains: rad9::ura4+ containing vector (>), pHRAD9-1(●) or pHRAD9-1 (Δ).

Figure 3A:
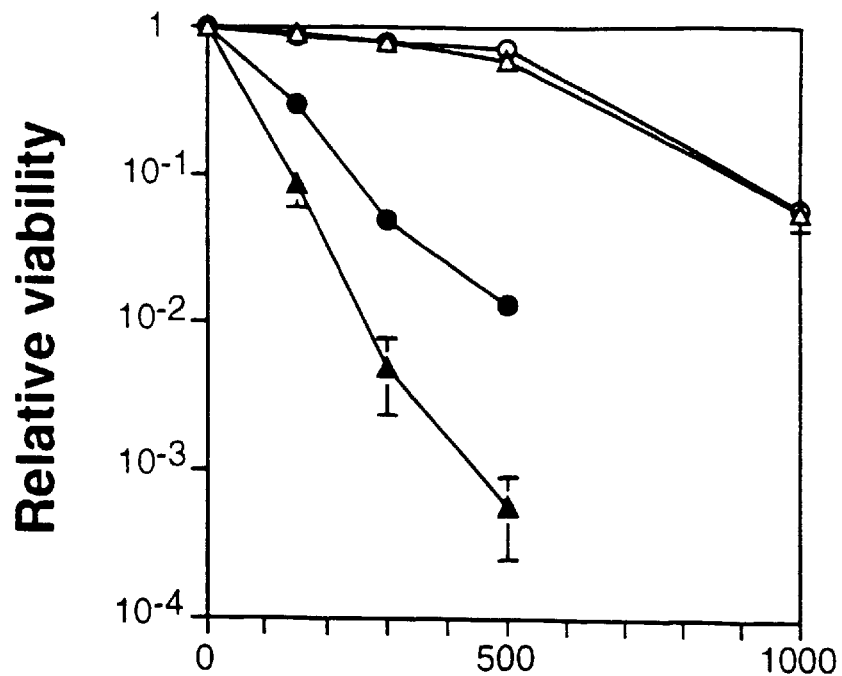
Figure 3B:
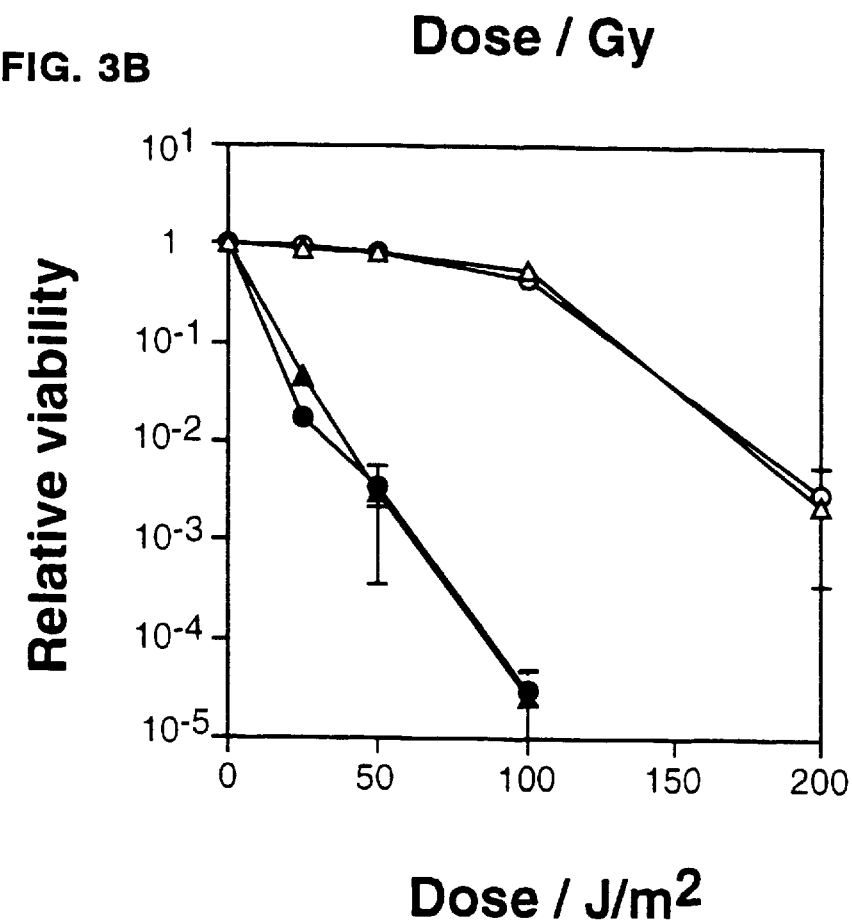

FIGS. 3A and 3B

Wildtype human homolog of RAD9 expression increases cell survival of rad9 null strains exposed to ionizing radiation, but not to UV light.

3A. Log phase *S. pombe* was exposed to the indicated γ radiation doses.

3B. UV light doses, and assayed for viability by the ability to form colonies. Strains: rad9+(Δ), rad9+[pHRAD9-1] (○), rad9::ura4+(>), rad9::ura4+[pHRAD9-1] (●).

Figure 4A:
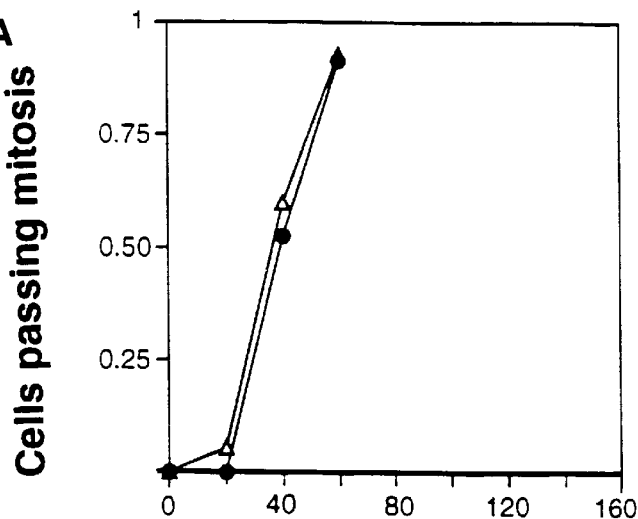
Figure 4B:
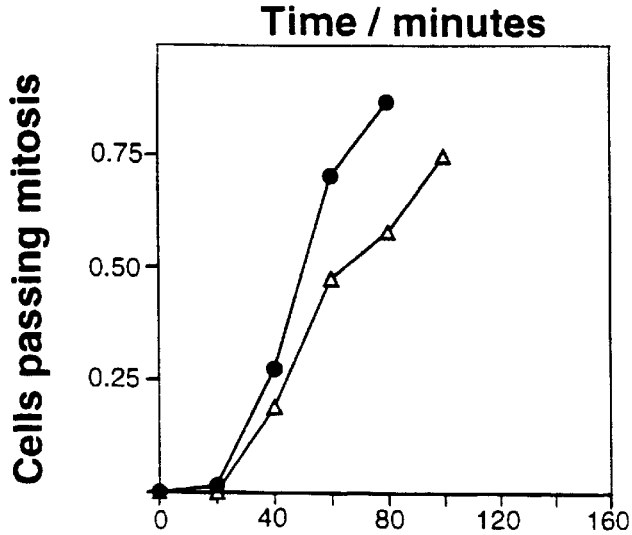
Figure 4C:
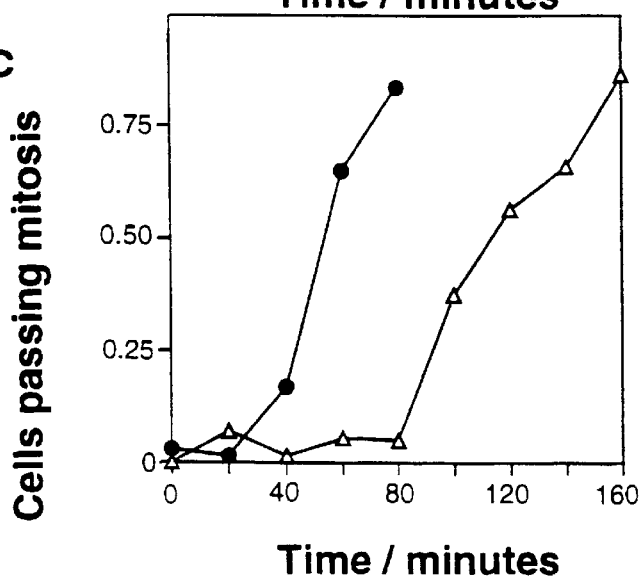

FIGS. 4A, 4B and 4C.

Wildtype human homolog of RAD9 expression partially restores mitotic entry delay in rad9 null strains exposed to ionizing radiation.

Strains were synchronized at the G2-M border by a 4 hour incubation at the restrictive temperature for cdc25-22. Synchronized cell populations were mock irradiated (●), or irradiated with 100 Gy ionizing radiation (Δ), and released to permissive temperature (time=0). At the indicated times after release, aliquots were fixed with ethanol. Cells were stained with propidium iodide, and scored under a fluorescence microscope for the fraction of binucleate cells, indicative of passage through mitosis.

4A. Transformation of a cdc25-22 rad9::ura4+ strain with control vector.

4B. Transformation of a cdc25-22 rad9::ura4+ strain with plasmids containing a wildtype human homolog of RAD9.

4C. Transformation of a cdc25-22 rad9::ura4+ strain with S. pombe rad9.

FIGS. 5A, 5B, 5C, 5D and 5E.

Wildtype human homolog of RAD9 is located at 11q13.1–11q13.2.

5A. FISH mapping of a metaphase spread with specific dual-chromatid staining of a Cy3-labeled genomic wildtype human homolog of RAD9 probe (red) to 11q13 on DAPI/AD (white-blue) stained normal human chromosomes.

5B. Enlarged version of chromosome 11 from two different metaphase spreads.

5C. DNA sequences analysis of the wildtype human homolog of RAD9 genomic clone used in FISH analysis identifies the location of an intron. The location of the primers used for PCR in sections C and D are indicated.

5D. PCR analysis using total human, mouse, or hamster genomic DNA, or DNA isolated from somatic cell hybrids containing a single human chromosome only, as indicated. This confirms the chromosomal location indicated by FISH analysis. The cDNA sequence of wildtype human homolog of RAD9 is designated Sequence ID No.: 4. Portions of the genomic DNA sequence of wildtype human homolog of RAD9 is designated Sequence ID No.: 5.

5E. PCR analysis sublocalizes wildtype human homolog of RAD9 to 11q13.1-11q13.2, as the genomic DNA is absent in a somatic cell hybrid containing 11q13.3-11q ter (11936), and present in three hybrids spanning the 11q13.1-11q13.2 region (11943, 13400, and 10482).

FIG. 6

Restriction map of pHRAD9-1.

DETAILED DESCRIPTION OF THE INVENTION

The invention provides an isolated nucleic acid which encodes a wildtype human homolog of RAD9. This invention also provides an isolated nucleic acid which encodes a mutant human homolog of RAD9. These isolated nucleic acids may be DNA, RNA, cDNA or genomic DNA. The DNA sequence of the wildtype human homolog of RAD9 has been deposited with the GenBank database which is a registered trademark of the National Institutes of Health. The Genbank database is managed and produced by the National Center for Biotechnology Information, National Library of Medicine. The DNA sequence of the wildtype human homolog of RAD9 was submitted to Genbank on Mar. 29, 1996 and assigned GenBank Accession Number U53174. This invention specifically provides an isolated nucleic acid having the sequence designated Sequence ID No.: 4 and encoding a wildtype human homolog of RAD9 which has the amino acid sequence designated Seq. ID No.: 1.

As used herein a wildtype human homolog of RAD 9 means a polypeptide which has an amino acid sequence identical to that present in a naturally-occurring form of RAD9. As used here a mutant human homolog of RAD9 means a polypeptide having an amino acid sequence which differs by one or more amino residues from any naturally occurring form, including deletions mutants containing less than all of the residues present in the wildtype polypeptide, substitution homologs wherein one or more residues are replaced by other residues, and addition homologs wherein on or more amino acid residues are added to a terminal or medial portion of the polypeptide.

The invention also provides a vector which encodes a wildtype human homolog of RAD9 or a mutant thereof, operatively linked to a promoter of RNA transcription which maybe, or is identical to, a bacterial, yeast, insect or mammalian promoter.

Numerous vector backbones known in the art as useful for expressing proteins may be employed. Such vectors include plasmid vectors, cosmid vectors, yeast artificial chromosomes (YAC), bacteriophage and eukaryotic viral DNA. For example, one such class of vectors comprises DNA elements derived from viruses such as bovine papilloma virus, polyoma virus, adenovirus, vaccinia virus, baculovirus, retroviruses (RSV, MMTV or MoMLV), Semliki Forest virus or SV40 virus. Such vectors may be obtained commercially or assembled from the sequences described by methods well-known in the art.

Figure 6:
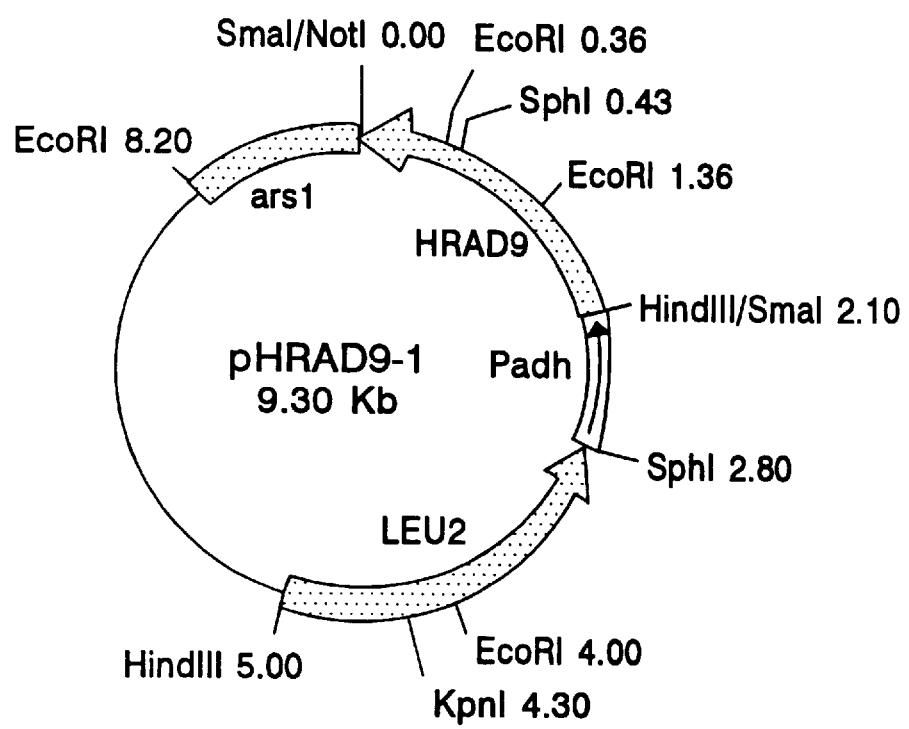

This invention specifically provides a plasmid designated pHRAD9-1. Plasmid pHRAD9-1 was made by cleaving DNA which encodes a wildtype human homolog of RAD9 with Hind III and Not I, creating blunt ends and inserting the DNA into the SmaI site of pART1 (FIG. 6). pHRAD9-1 was deposited on May 2, 1996 with the American Type Culture Collection (ATCC), 12301 Parklawn Drive, Rockville, Md. 20852, U.S.A., under the provisions of the Budapest Treaty For The International Recognition Of The Deposit Of Microorganisms For The Purposes Of Patent Procedure. pHRAD9-1 has been accorded ATCC Accession Number 97527.

This invention also provides a host vector system for the production of a polypeptide which comprises the vector in a suitable host cell. Suitable host cells include, but are not limited to, prokaryotic or eukaryotic cells, e.g. bacterial cells (including gram positive cells), yeast cells, fungal cells, insect cells and animal cells. Suitable animal cells include, but are not limited to, HeLa cells, Cos cells, CV1 cells and various primary mammalian cells. Numerous mammalian cells may be used as hosts, including, but not limited to, mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

This invention also provides a method of producing a polypeptide (e.g. a wildtype homolog of RAD9) which comprises growing a host vector system, as described above, under suitable conditions permitting production of the polypeptide and recovering the polypeptide so produced. Methods of recovering polypeptides produced in such host vector systems are well-known in the art and typically include steps involving cell lysis, solubilization, and chromatography.

This invention also provides a method of obtaining a polypeptide in purified form which includes (a) introducing a vector, as described above, into a suitable host cell; (b) culturing the resulting host cell so as to produce the polypeptide; (c) recovering the polypeptide produced in step (b); and (d) purifying the polypeptide so recovered. As discussed above, the vector may include a plasmid, cosmid, yeast artificial chromosome, bacteriophage or eukaryotic viral DNA. Also, the host cell may be a bacterial cell (including gram positive cells), yeast cell, fungal cell, insect cell or animal cell. Suitable animal cells include, but are not limited to HeLa cells, Cos cells, CV1 cells and various primary mammalian cells. Culturing methods useful for permitting transformed or transfected host cells to produce polypeptides are well known in the art as are methods for recovering polypeptides from such cells and for purifying the polypeptides.

Using the aforementioned method, this invention thus also provides purified wildtype human homologs of RAD9 and purified mutant human homologs of RAD9.

This invention also provides an oligonucleotide of at least 15 nucleotides capable of specifically hybridizing with a unique sequence of nucleotides within a nucleic acid which encodes a wildtype human homolog of RAD9 without hybridizing to any sequence of nucleotides within a nucleic acid which encodes a mutant human homolog of RAD9. These oligonucleotides may comprise DNA, RNA or modified nucleotides; all are well known in the art and may be made using standard methods such as automated synthesis.

Further, this invention provides an oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9.

Specifically this invention provides nucleic acids having a sequence complementary to the sequence of an isolated nucleic acid encoding a wildtype human homolog of RAD9 or one encoding a mutant thereof. Such oligonucleotides may be used in accordance with well known standard methods for known purposes, for example, to detect the presence in a sample of DNA which will hybridize thereto.

This invention also provides a method for determining whether a subject has radiosensitivity (i.e., whether a subject is sensitive to ionizing or ultraviolet radiation) which comprises (a) obtaining an appropriate nucleic acid sample from the subject; and (b) determining whether the nucleic acid sample from step (a) is, or is derived from, a nucleic acid which encodes a mutant human homolog of RAD9 so as to thereby determine whether a subject has radiosensitivity.

The nucleic acid sample in step (a) may be mRNA corresponding to the reverse transcript of the subject's genomic DNA encoding a mutant human homolog of RAD9 and the sample may be a sample containing genomic DNA from the subject treated so as to render it amendable to analysis, e.g. subject to restriction enzyme cleavage and electrophoretic separation.

The determination step (b) may comprise: (i) contacting the mRNA with a nucleic acid encoding a mutant human homolog of RAD9 or an oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9, under conditions permitting binding of the mRNA to the isolated nucleic acid or the oligonucleotide so as to form a complex; (ii) isolating the complex so formed; and (iii) identifying the mRNA in the isolated complex so as to thereby determine whether the mRNA is, or is derived from, a nucleic acid which encodes a mutant human homolog of RAD9. In this method, both the isolating of any complex formed and the identification of mRNA present in the complex are effected using standard methods well known in the art.

The determination step (b) may alternatively comprise: (i) contacting the nucleic acid sample of step (a) with the isolated nucleic acid encoding a mutant human homolog of RAD9 or an oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9 under conditions permitting binding of the nucleic acid sample to the nucleic acid or oligonucleotide so as to form a complex; (ii) isolating the complex so formed; and (iii) identifying the nucleic acid in the isolated complex so as to thereby determine whether the nucleic acid sample is, or is derived from, a nucleic acid which encodes a mutant human homolog of RAD9.

In order to facilitate identification of the nucleic acid from step (a) the isolated nucleic acid or oligonucleotide may be desirably labeled with a detectable marker such as a radioactive isotope, a fluorophor or an enzyme. In addition, the nucleic acid sample may be bound to a solid matrix before performing step (i).

Optimally, the determination step (b) may also comprise: (i) amplifying the nucleic acid present in the sample of step (a); and (ii) detecting the presence of the mutant human homolog of RAD9 in the resulting amplified nucleic acid. Such amplification may be effected, for example, by the polymerase chain reaction and may be particularly useful if the nucleic acid sample of step (a) is present in the sample at an otherwise undetectable or hardly detectable concentration.

In these methods, the nucleic acid sample of step (a) may comprise blood, sera or amniotic fluid treated to release or otherwise prepared to test the nucleic acids present. Also, the subject may be a fetus.

This invention also provides a method for treating a subject who is radiosensitive which comprises introducing an isolated nucleic acid which encodes a wildtype human homolog of RAD9, into the subject so as to thereby treat the subject who is radiosensitive. Examples of subjects for whom such treatment may be useful are subjects who have *Ataxia telangiectasia* or *Xeroderma pigmentosum*.

This invention also provides a method for predicting the effect of radiation therapy or chemotherapy, such as therapy involving radiomimetic cytotoxic drugs or DNA replication inhibitors, e.g. hydroxyurea, on a subject which comprises (a) obtaining an appropriate nucleic acid sample from the subject; and (b) determining whether the nucleic acid sample from step (a) is, or is derived from, a nucleic acid which encodes a mutant human homolog of RAD9 so as to thereby predict the effect of radiation therapy or chemotherapy on a subject.

The nucleic acid sample in step (a) of the preceding method may be mRNA corresponding to the reverse transcript of the subject's genomic DNA encoding a mutant human homolog of RAD9 and the determination step (b)

may comprise: (i) contacting the mRNA with a nucleic acid encoding a mutant human homolog of RAD9 or an oligonucleotide of at least 15 nucleotides capable of specifically hybridizing with a unique sequence within a nucleic acid which encodes a mutant human homolog of RAD9 without hybridizing to any sequence of nucleotides within a nucleic acid which encodes a wildtype human homolog of RAD9, under conditions permitting binding of the mRNA to the isolated nucleic acid or the oligonucleotide so as to form a complex; (ii) isolating the complex so formed; and (iii) identifying the mRNA in the isolated complex so as to thereby determine whether the mRNA is, or is derived from, a nucleic acid which encodes a mutant human homolog of RAD9.

The aforementioned determination step (b) may alternatively comprise: (i) contacting the nucleic acid sample of step (a) with the isolated nucleic acid encoding a mutant human homolog of RAD9 or the oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9, under conditions permitting binding of the nucleic acid sample to the nucleic acid or oligonucleotide so as to form a complex; (ii) isolating the complex so formed; and (iii) identifying the nucleic acid in the isolated complex so as to thereby determine whether the nucleic acid sample is, or is derived from, a nucleic acid which encodes a mutant human homolog of RAD9. In this method, both the isolating of any complex formed and the identification of mRNA present in the complex are effected using standard methods well known in the art.

Specific variations of the method involving, for example, immobilization of the nucleic acid sample may be employed similar to those described hereinabove for the method for determining whether a subject has radiosensitivity.

This invention also provides a method for detecting whether a subject has a predisposition to cancer which comprises: (a) obtaining an appropriate nucleic acid sample from the subject; and (b) determining whether the nucleic acid sample from step (a) is, or is derived, from a nucleic acid which encodes a mutant human homolog of RAD9 so as to thereby detect whether a subject has a predisposition to cancer.

The nucleic acid sample in step (a) of the preceding method may be mRNA corresponding to the reverse transcript of the subject's genomic DNA encoding a mutant human homolog of RAD9 and the determination step (b) may comprise: (i) contacting the mRNA with a nucleic acid encoding a mutant human homolog of RAD9 or an oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9, under conditions permitting binding of the mRNA to the isolated nucleic acid or the oligonucleotide so as to form a complex; (ii) isolating the complex so formed; and (iii) identifying the mRNA in the isolated complex so as to thereby determine whether the mRNA is, or is derived from, a nucleic acid which encodes a mutant human homolog of RAD9. In this method, both the isolating of any complex formed and the identification of mRNA present in the complex are effected using standard methods well known in the art.

The aforementioned determination step (b) may alternatively comprises: (i) contacting the nucleic acid sample of step (a) with the isolated nucleic acid encoding a mutant human homolog of RAD9 or the oligonucleotide of at least 15 nucleotides capable of specifically hybridizing with a unique sequence of nucleotides within a nucleic acid which encodes a mutant human homolog of RAD9 without hybridizing to any sequence of nucleotides within a nucleic acid which encodes a wildtype human homolog of RAD9, under conditions permitting binding of the nucleic acid sample to the nucleic acid or oligonucleotide so as to form a complex; (ii) isolating the complex so formed; and (iii) identifying the nucleic acid in the isolated complex so as to thereby determine whether the nucleic acid sample is, or is derived from, a nucleic acid which encodes a mutant human homolog of RAD9.

Specific variations of the method involving, for example, immobilization of the nucleic acid sample, may be employed similar to those described hereinabove for the method for determining whether a subject has radiosensitivity.

This invention also provides a method for preventing cancer in a subject who is radiosensitive which comprises: (a) recovering the subject's appropriate cells; (b) transforming these cells with the isolated nucleic acid which encodes a wildtype human homolog of RAD9; and (c) introducing the transformed cells from step (b) into the subject so as to thereby prevent cancer in the subject. In addition, the subject may be a mammal (e.g. human). Further the appropriate cells comprise somatic, bone marrow, liver, intestinal, germ, myocyte, endothelial, tumor and stem cells. Standard methods may be used to prevent cancer in a subject using this invention. Methods of recovering and of transforming cells are standard methods well known in the art.

This invention also provides a pharmaceutical composition which comprises a purified wildtype human homolog of RAD9 and a pharmaceutically acceptable carrier. This invention also provides a method of treating a subject who has cancer by administrating an effective amount of the pharmaceutical composition to the subject who has cancer. As used herein "effective amount" means an amount of the pharmaceutical composition effective to treat a subject who has cancer. Additionally, the subject may be sensitive to chemotherapeutic agents, such as chemotherapeutic agents which comprise radiomimetic cytotoxic drugs or DNA replication inhibitors, specifically hydroxyurea.

The pharmaceutical composition may be administered by topical, oral, aerosol, subcutaneous administration, infusion, intralesional, intramuscular, intraperitoneal, intratumoral, intratracheal, intravenous injection, or liposome-mediated delivery.

This invention also provides a method for treating a subject who has cancer which includes (a) recovering tumor cells from the subject; (b) introducing into the cells an oligonucleotide of at least 15 nucleotides capable of specifically hybridizing with a unique sequence of nucleotides within a nucleic acid which encodes a wildtype human homolog of RAD9 without hybridizing to any sequence of nucleotides within a nucleic acid which encodes a mutant human homolog of RAD9; (c) reintroducing the cells from step (b) into the subject; and (d) administrating an effective amount of a chemotherapeutic agent or radiation or both to the subject so as to thereby treat the subject. One skilled in the art is familiar with standard methods of recovering and transforming cells. As used herein "effective amount" means an amount of the chemotherapeutic agent or radiation or both effective to treat a subject who has cancer. Specifically tumor cells comprise brain cancer, breast cancer, cervical cancer, lung cancer, melanoma or renal carcinoma cells.

This invention also provides a transgenic, nonhuman mammal comprising a wildtype human or murine homolog of RAD9 gene. This invention also provides a transgenic, nonhuman mammal comprising a mutant human or murine homolog of the RAD9 gene. For example, the mammal may be a mouse.

This invention also provides a method for detecting the presence of human chromosomal region 11q13 in a sample of genomic DNA which includes: (a) contacting the sample with the isolated nucleic acid which encodes a wildtype human homolog of RAD9 or the oligonucleotide of at least 15 nucleotides capable of specifically hybridizing with a unique sequence of nucleotides within a nucleic acid which encodes a wildtype human homolog of RAD9 without hybridizing to any sequence of nucleotides within a nucleic acid which encodes a mutant human homolog of RAD9, under conditions permitting the formation of a complex between any genomic DNA present in the sample that is complementary to such nucleic acid or oligonucleotide; and (b) detecting the presence of any complex formed in step (a), the presence of such a complex indicating that the human chromosomal region 11q13 was present in the sample.

In order to facilitate the detection of the 11q13 human chromosomal region, the isolated nucleic acid or oligonucleotide may desirably be labeled with a detectable marker, such as a radioactive isotope, a fluorophor or an enzyme.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

Example 1

Materials and Methods

DNA sequence was determined using Sequenase Version 2 (U.S. Biochemicals), according to the instructions of the manufacturer. DNA oligonucleotides with complementary sequences to wildtype human homolog of RAD9 were synthesized throughout the length of the gene, and were used to prime DNA sequencing reactions. Sequences of the oligonucleotides used were as follows: F1, CTGTTCTGC-CCTTCTCT (Sequence ID No.: 6); F2, TGCAGAGTCAG-CAAAC (Sequence ID No.: 7); F3, CCAATGACGACAT-TGA (Sequence ID No.: 8); F4, CTTCCAGCAATACCAG (Sequence ID No.: 9); F5, TGCATTGCAACTTCGG (Sequence ID No.: 10); F6, AGGCTGAACCAAGAAC (Sequence ID No.: 11); F7, CGTTCCTACCTCTTAT (Sequence ID No.: 12); F8, GACAAGTTTTCCTTGC (Sequence ID No.: 13); F9, TCAAGAGACCAGATGG (Sequence ID No.: 14); T1, GTTTGCTGACTCTGCA (Sequence ID No.: 15); T2, AGAGAAGGGCAGAACAG (Sequence ID No.: 16); T3, CTGGTATTGCTGGAAG (Sequence ID No.: 17); T4, TCAATGTCGTCATTGG (Sequence ID No.: 18); T5, GTTCTTGGTTCAGCCT (Sequence ID No.: 19); T6, CCATCTGGTCTCTTGA (Sequence ID No.: 20); T7, GCAAGGAAAACTTGTC (Sequence ID No.: 21); T8, ATAAGAGGTAGGAACG (Sequence ID No.: 22). The nucleotide sequence of each strand of the wildtype human homolog of RAD9 gene was determined at least once. Amino acid sequences were aligned using the Genetic Computer Group Program Pileup and Pretty/Consensus.

S. pombe was cultured by standard techniques. S pombe transformations were performed according to the method of Okazaki, et al. (36). Complete genotypes of strains used are as follows: Sp348, h$^{-S}$ Leu1-32 ura4-294 ade6-216; sP349, H$^{-S}$ rad9::ura4+ leu1-32 ura4-294 ade6-216. Relative viability was determined by the ability to form colonies. Cells were cultured to mid-log phase, then hydroxyurea was added to the indicated concentration. Samples were removed at the indicated times after addition of hydroxyurea, and plated onto minimal selective media at the appropriate density. Plates were incubated for 3–6 days, until colonies were easily detectable. For determination of septation, cells were cultured in the same manner, but at the indicated times after hydroxyurea addition, cells were collected and fixed in 70% ethanol. Cells were washed once in 50 mM sodium citrate, then stained with 1 $\mu$g/m; calcofluor (Florescent Brightener 28, Sigma). The complete genotype of the strain used was: Sp296, h$^{-S}$ rad9::ura4+ leu1-32 ura4-D18 ade6-704. Control vector, pART1; pHRAD9-1, full length wildtype human homolog of RAD9 in pART1; pHRAD9-1, S. pombe rad9 in pART1. Data represent the average of three experiments, and error bars represent the standard deviation of the data (FIG. 2).

Cell culture and genotypes were as described for FIG. 3. γ irradiation was performed using a Gammacell 220 with a $^{60}$Co source, at a dose rate of 1 Gy/sec. UV light treatments were performed at 254 nm, with a dose rate of 2.68 J/m$^2$/sec. Data represent the average of three experiments, and error bars represent the standard deviation of the data.

Strains were grown as above to mid-log phase at the permissive temperature of 25° C. Cultures were then shifted to the restrictive temperature of 36° C. for 4 hours. Cells were irradiated in the 10 minutes prior to release from the G2-M block, using a Clinac 2100 C/D with a 6 MV beam, at a dose rate of 0.23 Gy/sec. At time=0, cells were released to permissive temperature, 25° C. At the indicated times, aliquots were removed and fixed with 70% ethanol. Cells were washed once with 50 mM sodium citrate, pH 7.0, and treated with 250 $\mu$g/ml Rnase A in 50 mM sodium citrate, pH 7.0, for 1 hour at 37° C. Cells were stained with 2.5 $\mu$g/ml propidium iodide, and examined under a confocal microscope. Binucleate cells were scored as having passed mitosis. Data represent the average of three experiments (FIGS. 4A, 4B and 4C).

The wildtype human homolog of RAD9 genomic clone was purified from a human placental DNA library in 1 Fix 11 (Stratagene), by in situ plaque hybridization. FISH was performed using established methods on methotrexate synchronized, phytohemagglutinin stimulated, normal peripheral blood lymphocytes (37). Suppression for 30 minutes with a mixture of sonicated human DNA (Sigma) and cot1 DNA (Gibco/BRL) was required to reduce the background. The stained slides were counterstained with DAPI and actinomycin D (for a DA-DAPI banding pattern), mounted in antifade medium and visualized utilizing a Zeiss Axioplan 2™ microscope. Approximately 30 metaphase spreads were examined for probe localization. At least one specific probe signal was present in more than 80% of the mitoses examined. Images were captured using a cooled CCD camera (Photometrics PXL1400). Digital alignment of the images from each fluor was done after registration calibration through a triple bandpass filter (FITC/Texas Red/DAPI) to minimize registration error, utilizing commercial software (Electronic Photography, Biological Detection Inc., Pittsburgh, Pa.). The figure was prepared using Adobe Photoshop (Adobe Systems Inc.) and printed on a Tektronics Phaser 440 dye-sublimation printer.

Figure 5A:
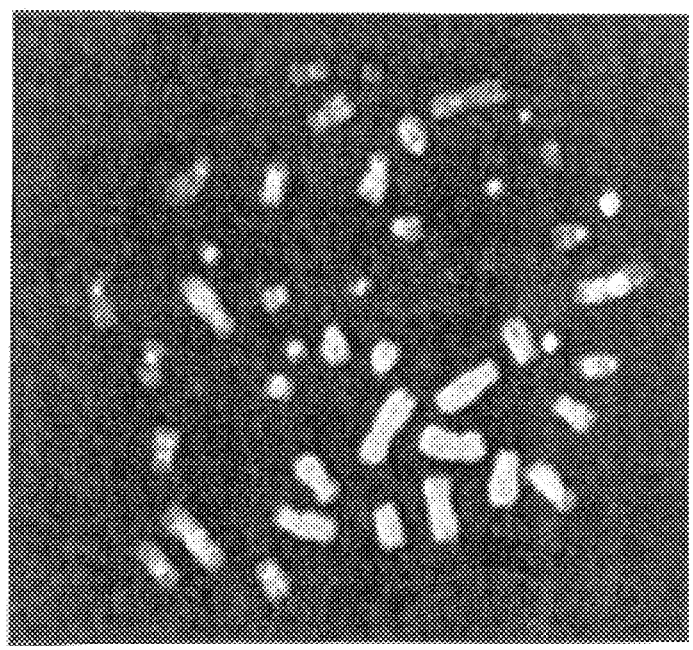
Figure 5B:
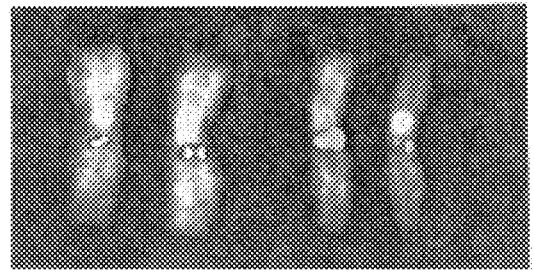

DNA sequencing was performed as described in FIG. 1, using the purified genomic DNA as template, and the leftward oligonucleotide depicted in FIG. 5B. The sequence of the oligonucleotide was: o957, CATGGTGACTGAGAT-GTG (Sequence ID No. 23). PCR reactions were performed using DNA obtained from the Coriell Cell Repositories (Mapping panel #2 mini, and the Regional mapping panel for chromosome 11) (38, 39). PCR reactions were carried out using 1 µg DNA, 100 pmol primers, 0.2 mM each dATP, dCTP, dGTP, and dTTP, 2.5 units Taq polymerase, 1.5 mM MgCl$_2$, and 1× Taq buffer (BRL), in a total volume of 100 µl. PCR was performed for 35 cycles, each consisting of 1 minute at 94° C., 30 seconds at 57° C., and 2 minutes at 72° C., with a 5 minute preincubation at 95° C., 30 seconds at 57° C., and 2 minutes at 72° C., with a 5 minute preincubation at 95° C., and a final extension of 10 minutes at 72° C. The oligonucleotides used to prime the reaction were: o957 (Sequence ID No.: 23); o980, CCAAAAATCCT-TGATGGTGAAGATGGCGGGCCTCCCTG-GAGCATCAAAAT (Sequence ID No.: 24). In Part D, the subregions of chromosome 11 represented by the various cell lines are as follows: 11936, 11q13.3.-11q ter; 11943, 11p13-11q ter; 13400, 11p ter-11q24.2; 10482, 11p ter-11q23.3; 11944, 11p cen-11p ter.

Discussion

A human homologue of the fission yeast rad9 checkpoint control gene has been identified. Also, the ability of this gene to partially complement hydroxyurea sensitivity, radiosensitivity, and the checkpoint defects of rad9 null yeast has been shown.

A search of the best data base revealed a sequence expressed in human infant brain (Genbank accession number R18275) that predicted a 43 amino acid region with 34% identical and 60% similar amino acid composition when compared to the S. octosporus rad9 gene product. The clone was obtained from the I.M.A.G.E. Consortium and DNA sequence analysis of the 1.6 kb insert revealed that the protein coding region shared homology with the carboxyl terminal half of the S. pombe and S. octosporus Rad9 proteins, suggesting that the cDNA was not full length. Therefore, the original human cDNA library (11) was screened for a full length version of the wildtype human homolog of RAD9 gene, using the truncated clone to generate probes for in situ colony hybridization. Examination of 150,000 colonies yielded 11 clones, of which one contained a 2.1 kb insert. Sequence analysis indicated that this clone contained a 76 bp 5' untranslated region, a 1176 bp coding region, and an 850 bp 3' untranslated region. The open reading frame encodes a protein of 391 amino acids, which shares sequence similarity to the fission yeast Rad9 proteins (FIGS. 1A and 1B). Wildtype human homolog of RAD9 is 25% identical and 52% similar at the amino acid level to S. pombe Rad9, and 27% identical and 54% similar to the corresponding protein from S. octosporus. The predicted Rad9 proteins exhibit sequence similarity over their entire lengths, including the amino terminal end, suggesting that the isolated human cDNA is full length. No motifs indicative of function are present in any of the Rad9 proteins, though a single phosphorylation consensus site for each of casein kinase 11 and protein kinase C have been conserved among the three proteins.

The cDNA of the wildtype human homolog of RAD9 was subcloned into the S. pombe expression vector pART1 (12) (FIG. 6), and introduced into rad+ and rad9::ura4+ cells to assess the rescue of defects caused by loss of rad9 function.

Wildtype human homolog of RAD9 restores resistance of rad9::ura4+ cells to transient exposure to the DNA synthesis inhibitor hydroxyurea (FIG. 2A). Expression of wildtype human homolog of RAD9 has no effect on the survival of wild-type cells exposed to hydroxyurea (FIG. 2A). Furthermore, the presence of the control pART1 vector does not influence the hydroxyurea sensitivity of either rad+ or rad9::ura4+ cells. The wildtype human homolog of RAD9 subclone, the S. pombe rad9 gene, and control pART1 vector were subsequently transformed into rad9::ura4+ mutant cells and these strains were assayed for changes in mitotic entry in response to Hydroxyurea treatment. In cell populations transformed with control pART1 vector, there was an accumulation of septated cells, as the checkpoint deficient strain entered mitosis (FIG. 2B). In contrast, neither the strains carrying wildtype human homolog of RAD9 nor rad9 expressing plasmids exhibited this accumulation of septated cells (FIG. 2B). In wild-type cells there is virtually no septation 4 hours after addition of hydroxyurea. The fact that there was approximately 20% septation in the rad9::ura4+ strains rescued by either the wildtype human homolog of RAD9 or rad9 genes is probably due to the high spontaneous rate of plasmid loss in S. pombe; cells which have lost the rad9 containing plasmid remain viable for a period of time, but would be functionally checkpoint deficient. In all cases, parallel samples which were not treated with Hydroxyurea exhibited 15–20% septation at the final time point.

Wildtype human homolog of RAD9 expression also confers a moderate level of resistance to radiation in rad9::ura4+ mutant cells (FIG. 3A). The same strains described for FIG. 2A were treated with various doses of ionizing radiation or UV light, and plated to assay surviving cells. Wildtype human homolog of RAD9 expression in rad9::ura4+ strains leads to partial restoration of resistance to radiation, while expression of wildtype human homolog of RAD9 in rad+ cells has no significant effect on survival (FIG. 3A). Expression of wildtype human homolog of RAD9 in rad+ or rad9::ura4+ mutant cells does not alter sensitivity to UV light (FIG. 3B).

Wildtype human homolog of RAD9 expression also induces a detectable mitotic entry delay after exposure to ionizing radiation, which is lost in the rad9::ura4+ mutant (FIGS. 4A, 4B and 4C). This delay is an indication of a weak rescue of the checkpoint deficiency in rad9::ura4+ mutants bearing the wildtype human homolog of RAD9 plasmid, as reflected by the moderate increase in resistance to ionizing radiation shown by these cells (FIG. 3A). Alternatively, this delay could be interpreted as representing a reduced rate of mitotic entry by these cells. However, a reduced rate of mitotic entry is unlikely, as rad+ cells containing wildtype human homolog of RAD9 show radiation resistance and cycling profiles indistinguishable from those observed for cells carrying either the pART1 control vector, or carrying no plasmid. Furthermore, the pART1 control vector does not confer radiation resistance upon rad9::ura4+ cells.

The different degrees of complementation of S. pombe mutant cells by the human cDNA may reflect differential requirements of rad9 for achieving increased survival or induction of checkpoint control after exposure to Hydroxyurea and each type of radiation. The rad9 dependent checkpoints in S. pombe respond to signals both during S phase, and in G2 (4,5). The efficient rescue of one, but not both, of these defects of wildtype human homolog of RAD9 mediates the cell cycle delay in response to incomplete DNA replication, but not DNA damage. Alternatively, if unique protein complexes mediate DNA damage and incomplete DNA replication signals, wildtype human homolog of RAD9 may function more efficiently with the latter complex.

Even in the absence of exogenous DNA damage, defects in cell cycle checkpoints lead to genomic instability, as demonstrated for the G2-M checkpoint in *S. cerevisiae* rad9 mutants (2), and at the G1-S checkpoint in p53 or ATM deficient mammalian cells (9, 10, 13, 14, 15). The resulting widespread genomic abnormalities are typical of cancer cells (17). As noted above, the rad3 gene is homologous to the human ATM gene, and mutations in ATM lead to an increased incidence of cancer (6, 17, 18). AT patients are at an elevated risk for developing numerous tumor types, and even AT carriers exhibit an elevated risk of developing cancer (17, 18). Both the ATM and p53 genes not only regulate cell cycle checkpoints (12, 15), but also act as tumor suppressors (17, 18, 24, 25, 26). It is likely that other human checkpoint genes will also act as tumor suppressors. For this reason, the chromosomal location of wildtype human homolog of RAD9 was determined as a first step towards determining whether this gene is a human tumor suppressor.

Figure 5D:
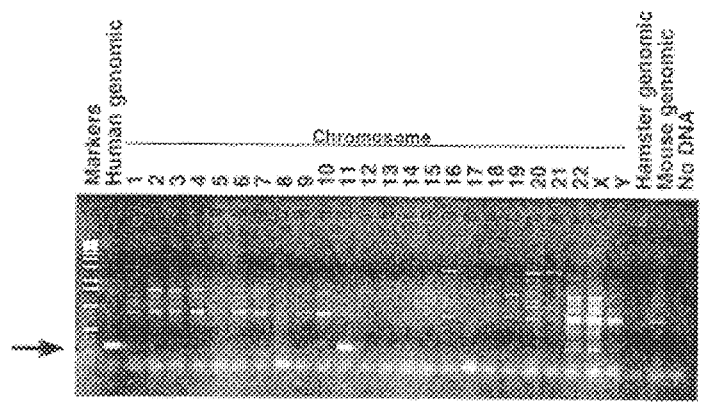
Figure 5E:
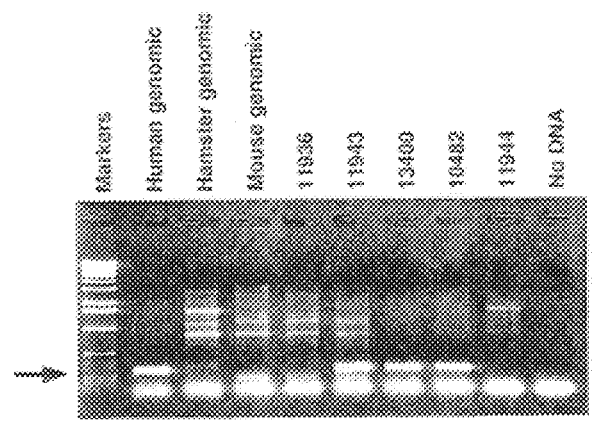

Wildtype human homolog of RAD9 was localized to chromosomal region 11q13.1-11q13.2 (FIGS. 5A, 5B, 5C, 5D and 5E). A genomic clone of wildtype human homolog of RAD9 was identified from a human placental DNA library by in situ hybridization to the original wildtype human homolog of RAD9 cDNA clone. This genomic clone was used as a probe for fluorescence in situ hybridization to metaphase chromosomes, and the chromosomal location was identified as 11q13 (FIG. 5A). Limited DNA sequence analysis of this genomic wildtype human homolog of RAD9 clone reveals the presence of an intron in the insert, confirming that the bona fide wildtype human homolog of RAD9 genomic sequence was isolated, and not a processed wildtype human homolog of RAD9 pseudogene (FIG. 5B). Two oligonucleotides directed against wildtype human homolog of RAD9 were used to prime PCR reactions on the genomic clone, total genomic DNA, and on genomic DNA from human X rodent somatic cell hybrid lines. The 275 nucleotide PCR product is only generated in samples containing human chromosome 11 DNA, confirming the chromosomal assignment made by FISH (FIG. 5C). Further PCR analysis sublocalizes wildtype human homolog of RAD9 to 11q13.1-11q13.2. The 275 nucleotide PCR product indicative of the genomic DNA is present in three hybrids spanning the 11q13.1-11q13.2 region, but absent from a somatic cell hybrid containing 11q13.3-11q ter (FIG. 5D). Furthermore, the 3' end of the wildtype human homolog of RAD9 cDNA contains sequences from the 3' untranslated region of a human type 1 phosphatase gene, oriented opposite to the direction of translation of wildtype human homolog of RAD9. This phosphatase has previously been mapped to chromosome 11q13 (28), providing independent confirmation of the assigned map location.

The 11q13 region contains at least two tumor suppressor loci, the most prominent of which is MEN1, which is responsible for type 1 multiple endocrine neoplasia (28).

The type 1 phosphatase which is located near wildtype human homolog of RAD9 has been excluded as a candidate for the MEN1 gene by fine resolution mapping data (27, 29, 30, 31), suggesting that the wildtype human homolog of RAD9 should also be excluded from consideration as the causative gene for this cancer syndrome. The presence of a second tumor suppressor locus in this region is suggested by studies on cervical cancer derived cell lines (33), and wildtype human homolog of RAD9 can not be excluded as a candidate for this gene.

Overall, these results demonstrate that the wildtype human homolog of RAD9 gene can functionally complement some of the checkpoint defects of *S. pombe* rad9::ura4+ cells, suggesting that fission yeast rad9-dependent G2 checkpoint pathways, which promote radiation and hydroxyurea resistance are conserved at the molecular level in humans. The extensive genetic information known about G2 checkpoint control mechanisms in yeast will be invaluable towards defining parallel human pathways important for modulating the response of cells to DNA damage or the inhibition of DNA replication.

Example 2

Mice can be made with an alteration in their genome, specifically at the RAD9 gene site. Standard methods may be used to alter the genome. These methods are well known in the art (40, 41).

One such process to achieve this goal involves disrupting the wildtype mouse or human homolog of RAD9 in vitro, then introducing the altered gene into mouse embryonal stem cells in such a way as to target integration into the corresponding genomic region. This process can be performed twice such that both copies of the wildtype homolog of RAD9 can be replaced by the altered, knock-out version. These modified cells can be introduced into blastocysts which will be allowed to develop into chimeric adults. Mice bearing the altered RAD9 gene and capable of transmitting this gene to their progeny will be mated to each other to generate homozygous mutant RAD9 animals.

Alternatively, a plasmid capable of producing a RAD9 antisense RNA can be introduced into the embryonal stem cells. These cells can be subsequently introduced into mouse blastocyts, and then allowed to develop into adult mice which are unable to translate RAD9 RNA into protein.

Example 3

Antisense RNA technology can be used to create mice, or mouse or human cell lines incapable of translating RAD9 RNA into protein. Standard methods may be used to create an antisense oligonucleotide to the human homolog of RAD9. These methods are well known in the art (42).

Specifically, part or all of a wildtype homolog of RAD9 is ligated adjacent to a mammalian promoter in the opposite orientation. The promoter and other replicatory mechanisms inside the cell will transcribe a human homolog of RAD9 noncoding, nonsense strand. This strand will bind with the coding mRNA which is normally synthesized to form a complex. Due to the formation of this complex, the antisense strand prevents the translation of the coding mRNA into protein.

REFERENCES

1. Weinert, T. A. and L. H. Hartwell (1988) *Science* 241: 317–322.
2. Weinert, T. A. and L. H. Hartwell (1990) *Mol Cell Biol* 10: 6554–6564.
3. Rowley, R., et al. (1992) *Embo J* 11: 1335–1342.
4. al-Khodairy, F. and A. M. Carr (1992) *Embo J* 11: 1343–1350.
5. Enoch, T., et al. (1992) *Genes Dev* 6: 2035–2046.
6. Savitsky, K., et al. (1995) *Science* 268: 1749–1753.
7. Savitsky, K., et al. (1995) *Hum Mol Gen*, 2025–2032.
8. Taylor, A. M. R., et al., (1975) *Nature* 258: 427–429.
9. Painter, R. B. and B. R. Young (1980) *Proc Natl Acad Sci U.S.A.* 77: 7315–7317.
10. F. P. Imray, C. Kidson, (1983) *Mutat Res* 112: 369–382.
11. Soares, M. B., et al. (1994) *Proc Natl Acad Sci U.S.A.* 91: 9228–9232.
12. McLeod, M., et al. (1987) *Embo J* 6: 729–736.
13. Yin, Y., et al. (1992) *Cell* 70: 937–48.

14. Livingston, L. R., et al. (1992) *Cell* 70, 923–935.
15. Pandita, T. K., et al. (1995) *Cytogenet Cell Genet* 71: 86–93.
16. Nowell, P. C. (1976) *Science* 194: 23–28.
17. Swift, M., et al. (1991) *N Engl. J. Med* 325: 1831–1836.
18. Swift, M., et al. (1987) *N Engl J Med* 316: 1289–1294 (1987).
19. Kastan, M. B., et al. (1991) *Cancer Res* 51: 6304–6311.
20. Kastan, M. B., et al. (1992) *Cell* 71: 587–597.
21. Kuerbitz, S. J., et al. (1992) *Proc Natl Acad Sci U.S.A.* 89: 7491–7495.
22. O'Connor, P. M., et al. (1993) *Cancer Res* 53: 4776–80.
23. Dulic, V., et al. (1994) *Cell* 76: 1013–1023.
24. Malkin, D., et al. (1990) *Science* 250: 1233–1238.
25. Srivastava, S., et al. (1990) *Nature* 348: 747–749.
26. Donehower, L. A. et al., (1992) *Nature* 356: 215–221.
27. Barker, H. M., et al. (1990) *Genomics* 7: 159–166.
28. Larsson, C., et al. (1988) *Nature* 332: 85–87.
29. Larsson, C., et al. (1992) *Hum Genet* 89: 187–193.
30. Larsson, C., et al. (1994) *Endocrinol Metab Clin North Am* 23: 67–79.
31. Weber, G., et al. (1994) *Hum Mol Genet* 3: 1775–1781.
32. Jesudasan, R. A., et al. (1995) *Am J Hum Genet* 56: 705–715.
33. H. B. Lieberman (1995) *Genetics* 141: 107–117.
34. Higgins, D. G., et al. (1989) *Comput Appl Biosci* 5: 151–153.
35. Leupold, U. (1970) *Meth Cell Physiol* 4: 169–177.
36. Okazaki, K., et al. (1990) *Nucleic Acids Res* 18: 6485–6489.
37. Demetrick, D. J. (1995) The Cell Cycle: A Laboratory Handbook, M. Pagano, Ed. (Springer Verlag Press) pp.29–45.
38. Dubois, B. L., et al. (1993) *Genomics* 16: 315–319.
39. Drwinga, H. L., et al. (1993) *Genomics* 16: 311–314.
40. Duyao, M. P., et al. (1995) *Science* 269: 407–410.
41. Joyner, A. L. and F. Guillemot (1994) *Current Opinion in Neurobiology* 4: 37–42.
42. Griffin, E. F. and H. Harris (1992) *J. Cell Science* 102: 799–805.

---

What is claimed is:

1. An isolated nucleic acid which encodes a wildtype human homolog of RAD9 having the amino acid sequence designated SEQ ID NO 1.

2. An isolated nucleic acid having the sequence designated SEQ ID NO 4.

3. The isolated nucleic acid of claim 1 or 2, wherein the nucleic acid is DNA.

4. The isolated nucleic acid of claim 1 or 2, wherein the nucleic acid is RNA.

5. The isolated nucleic acid of claim 3, wherein the nucleic acid is cDNA.

6. A vector comprising the isolated nucleic acid of claim 1 or 2 operatively linked to a promoter of RNA transcription.

7. The vector of claim 6, wherein the promoter comprises a bacterial, yeast, insect or mammalian promoter.

8. The vector of claim 6, further comprising plasmid, cosmid, yeast artificial chromosome (YAC), bacteriophage or eukaryotic viral DNA.

9. A host vector system for the production of a polypeptide which comprises the vector of claim 6 in a suitable host.

10. The host vector system of claim 9, wherein the suitable host comprises a prokaryotic or eukaryotic cell.

11. The host vector system of claim 10, wherein the prokaryotic cell comprises a bacterial cell.

12. The host vector system of claim 10, wherein the eukaryotic cell comprises an yeast, insect, plant or mammalian cell.

* * * * *

UNITED STATES PATENT AND TRADEMARK OFFICE
CERTIFICATE OF CORRECTION

PATENT NO. : 5,882,862
DATED : March 19, 1999
INVENTOR(S) : Howard B. Lieberman, Kevin M. Hopkins and Scott K. Davey It is certified that error appears in the above-identified patent and that said Letters Patent is hereby corrected as shown below:

Title page,
Item [19], under United States Patent, "Davey et al." should read -- Lieberman et al. --.
Item [75], following INID Code, "Inventors: Scott K. Davey, Ontario, Canada; Howard B. Lieberman, Tenafly; Kevin M. Hopkins, Fort Lee, both of N.J." should read -- Inventors: Howard B. Lieberman, Tenafly, New Jersey; Kevin M. Hopkins, Fort Lee, New Jersey; Scott K. Davey, Ontario Canada --.
Item [56], References Cited, PUBLICATIONS, "rad9" should read -- *rad9* --,
Lieberman, H.B., et al. reference, "rad9" should read -- *rad9* --,
Lieberman, H.B. and K.M. Hopkins reference, "rad9" should read -- *rad9* --, and
Lieberman, H.B. reference, "rad9" should read -- *rad9* --.

Column 1,
Line 19, "rad9" should read -- *rad9* --.
Line 26, "rad9" should read -- *rad9* --.
Line 25, "rad1, rad3, rad9, rad17, or hus1" should read
-- *rad1, rad3, rad9, rad17,* or *hus1* --.
Line 33, "ATM" should read -- *ATM* --.
Line 34, "rad9" should read -- *rad9* --.
Line 35, "ATM" should read -- *ATM* --.

Column 2,
Line 26, "rad9" should read -- *rad9* --.
Line 27, "rad9" should read -- *rad9* --.
Line 34, "rad9" should read -- *rad9* --.
Line 46, "rad9" should read -- *rad9* --.
Line 53, "rad9+ (Δ), rad9+" should read -- *rad9+ (Δ), ura9+* --.
Line 53, "rad9 :: ura4+ (›)" should read -- *rad9 : ura4+ (›)* --.
Line 54, "rad9 :: ura4+" should read -- *rad9 : ura4+* --.
Line 60, "rad9 :: ura4+" should read -- *rad9 : ura4+* --.
Line 64, "rad9" should read -- *rad9* --.

Column 3,
Line 2, "rad9+ (Δ), rad9+" should read -- *rad9+ (Δ), ura9+* --.
Line 3, "rad9 :: ura4+ (›)" should read -- *rad9 : ura4+ (›)* --.
Line 3, "rad9 :: ura4+" should read -- *rad9 : ura4+* --.
Line 9, "cdc" should read -- *cdc* --.
Line 18, "cdc" should read -- *cdc* --.
Line 18, "rad9 :: ura4+" should read -- *rad9 : ura4+* --.
Line 20, "cdc" should read -- *cdc* --.

UNITED STATES PATENT AND TRADEMARK OFFICE
CERTIFICATE OF CORRECTION

PATENT NO. : 5,882,862
DATED : March 19, 1999
INVENTOR(S) : Howard B. Lieberman, Kevin M. Hopkins and Scott K. Davey It is certified that error appears in the above-identified patent and that said Letters Patent is hereby corrected as shown below:

Column 3 (continued),
Line 20, "rad9 :: ura4+" should read -- *rad9 : ura4+* --.
Line 21, "RAD9" should read -- *rad9* --.
Line 22, "cdc" should read -- *cdc* --.
Line 22, "rad9 : : ura4+" should read -- *rad9 : : ura4+* --.
Line 30, "RAD9" should read -- *rad9 (Hrad9)* --.

Column 4,
Line 8, "RAD 9" should read -- RAD9 --
Line 42, "May 2, 1996" should read -- May 15, 1998 --
Lines 43-44, "12301 Parklawn Drive, Rockville, Md. 20852" should read -- Manassas, VA 20110-2209 --
Line 48, "97527." should read -- 209871. --

Column 10,
Line 2, "sP349" should read -- Sp349 --.
Line 2, "Leul-32 ura4-294 ade6-216" should read -- *Leul-32 ura4-294 ade6-216* --.
Line 3, "rad9 : : ura4+ leul-32 ura4-294 ade6-216" should read -- *rad9 : : ura4+ leul-32 ura4-294 ade6-216* --.
Line 16, "rad9 : : ura4+leul-32 ura4-D18 ade6-704" should read -- *rad9 : : ura4+ leul-32 ura4-D18 ade6-704* --.
Line 18, "rad9" should read -- *rad9* --.
Line 45, "in situ" should read -- *in situ* --.

Column 11,
Line 24, "rad9" should read -- *rad9* --.
Line 27, "rad9" should read -- *rad9* --.
Line 33, "rad9" should read -- *rad9* --.
Line 42, "in situ" should read -- *in situ* --.
Line 62, "rad9 : : ura4+" should read -- *rad9 : : ura4+* --.
Line 63, "rad9" should read -- *rad9* --.
Line 65, "rad9 : : ura4+" should read -- *rad9 : : ura4+* --.

Column 12,
Line 3, "rad+" should read -- *rad+* --.
Line 4, "rad9 : : ura4+" should read -- *rad9 : : ura4+* --.
Line 5, "rad9" should read -- *rad9* --.
Line 6, "rad9 : : ura4+" should read -- *rad9 : : ura4+* --.
Line 12, "rad9" should read -- *rad9* --.

UNITED STATES PATENT AND TRADEMARK OFFICE
CERTIFICATE OF CORRECTION

PATENT NO. : 5,882,862
DATED : March 19, 1999
INVENTOR(S) : Howard B. Lieberman, Kevin M. Hopkins and Scott K. Davey It is certified that error appears in the above-identified patent and that said Letters Patent is hereby corrected as shown below:

Column 12 (continued),
Line 16, "rad9 : : ura4+" should read -- *rad9 : : ura4+* --.
Line 18, "rad9" should read -- *rad9* --.
Line 25, "rad9 : : ura4+" should read -- *rad9 : : ura4+* --.
Line 29, "rad9 : : ura4+" should read -- *rad9 : : ura4+* --.
Line 31, "rad+" should read -- *rad+* --.
Line 33, "rad+" should read -- *rad+* --.
Line 34, "rad9 : : ura4+" should read -- *rad9 : : ura4+* --.
Line 40, "rad9 : : ura4+" should read -- *rad9 : : ura4+* --.
Line 51, "rad9 : : ura4+" should read -- *rad9 : : ura4+* --.
Line 56, "rad9" should read -- *rad9* --.

Column 13,
Line 1, "rad9" should read -- *rad9* --.
Line 3, "ATM" should read -- *ATM* --.
Line 5, "rad3" should read -- *rad3* --.
Line 6, "ATM" should read -- *ATM* --.
Line 10, "ATM" should read -- *ATM* --.
Line 10, "p53" should read -- *p53* --.
Line 21, "in situ" should read -- *in situ* --.
Line 23, "in situ" should read -- *in situ* --.
Line 55, "MEN1" should read -- *MEN1* --.
Line 66, "rad9 : : ura4+" should read -- *rad9 : : ura4+* --.
Line 66, "rad9" should read -- *rad9* --.

Column 14,
Line 14, "in vitro" should read -- *in vitro* --.

Column 31,
Line 3, "RAD9having" should read -- RAD9 having --

UNITED STATES PATENT AND TRADEMARK OFFICE
CERTIFICATE OF CORRECTION

PATENT NO.    : 5,882,862
DATED         : March 19, 1999
INVENTOR(S)   : Howard B. Lieberman, Kevin M. Hopkins and Scott K. Davey It is certified that error appears in the above-identified patent and that said Letters Patent is hereby corrected as shown below:

Column 32,
Following claim 12, add -- Claim 13. The isolated nucleic acid of claim 3, wherein the nucleic acid is genomic DNA. --
Following claims 12 and 13, add -- Claim 14. The vector of claim 6 designated pHRAD9-1 (ATCC Accession Number 209871). --

Signed and Sealed this

Sixteenth Day of July, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 391 amino acids
        ( B ) TYPE: amino acid
        ( C ) STRANDEDNESS: single
        ( D ) TOPOLOGY: linear ( i i ) MOLECULE TYPE: Amino Acid ( x i ) SEQUENCE DESCRIPTION: SEQ ID NO: 1:

```
Met Lys Cys Leu Val Thr Gly Gly Asn Val Lys Val Leu Gly Lys Ala
 1               5                  10                  15

Val His Ser Leu Ser Arg Ile Gly Asp Glu Leu Tyr Leu Glu Pro Leu
            20                  25                  30

Glu Asp Gly Leu Ser Leu Arg Thr Val Asn Ser Ser Arg Ser Ala Tyr
        35                  40                  45

Ala Cys Phe Leu Phe Ala Pro Leu Phe Phe Gln Gln Tyr Gln Ala Ala
    50                  55                  60

Thr Pro Gly Gln Asp Leu Leu Arg Cys Lys Ile Leu Met Lys Cys Phe
65                  70                  75                  80

Leu Ser Val Phe Arg Ser Leu Ala Met Leu Glu Lys Thr Val Glu Lys
                85                  90                  95

Cys Cys Ile Ser Leu Asn Gly Arg Ser Ser Arg Leu Val Val Gln Leu
               100                 105                 110

His Cys Lys Phe Gly Val Arg Lys Thr His Asn Leu Ser Phe Gln Thr
           115                 120                 125

Cys Glu Ser Leu Gln Ala Val Phe Asp Pro Ala Ser Cys Pro His Met
       130                 135                 140

Leu Arg Ala Pro Ala Arg Val Leu Gly Glu Ala Val Leu Pro Phe Ser
145                 150                 155                 160

Pro Ala Leu Ala Glu Val Thr Leu Gly Ile Gly Arg Gly Arg Arg Val
                165                 170                 175
```

-continued

```
Ile Leu Arg Ser Tyr His Glu Glu Glu Ala Asp Ser Thr Ala Lys Ala
            180                 185                 190

Met Val Thr Glu Met Cys Leu Gly Glu Glu Asp Phe Gln Gln Leu Gln
            195                 200                 205

Ala Gln Glu Gly Val Ala Ile Thr Phe Cys Leu Lys Glu Phe Arg Gly
    210                 215                 220

Leu Leu Ser Phe Ala Glu Ser Ala Asn Leu Asn Leu Ser Ile His Phe
225                         230                 235                 240

Asp Ala Pro Gly Arg Pro Ala Ile Phe Thr Ile Lys Asp Ser Leu Leu
                245                 250                 255

Asp Gly His Phe Val Leu Ala Thr Leu Ser Asp Thr Asp Ser His Ser
            260                 265                 270

Gln Asp Leu Gly Ser Pro Glu Arg His Gln Pro Val Pro Gln Leu Gln
        275                 280                 285

Ala His Ser Thr Pro His Pro Asp Asp Phe Ala Asn Asp Asp Ile Asp
    290                 295                 300

Ser Tyr Met Ile Ala Met Glu Thr Thr Ile Gly Asn Glu Gly Ser Arg
305                         310                 315                 320

Val Leu Pro Ser Ile Ser Leu Ser Pro Gly Pro Gln Pro Pro Lys Ser
                325                 330                 335

Pro Gln Pro His Ser Glu Glu Glu Asp Glu Ala Glu Pro Ser Thr Val
            340                 345                 350

Pro Gly Thr Pro Pro Pro Lys Lys Phe Arg Ser Leu Phe Phe Gly Ser
        355                 360                 365

Ile Leu Ala Pro Val Arg Ser Pro Gln Gly Pro Ser Pro Val Leu Ala
    370                 375                 380

Glu Asp Ser Glu Gly Glu Gly
385                 390
```

( 2 ) INFORMATION FOR SEQ ID NO:2:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: Amino Acid ( x i ) SEQUENCE DESCRIPTION: SEQ ID NO:2:

```
Met Glu Phe Val Val Ser Asn Thr Asn Leu Arg Asp Leu Ser Arg Ile
1               5                   10                  15

Phe Leu Asn Leu Ser Arg Ile Asp Asp Ala Val Asn Trp Glu Ile Asn
            20                  25                  30

Lys Asp Gln Leu Ile Leu Thr Thr Leu Asn Ser Ser Arg Ser Gly Phe
        35                  40                  45

Gly Lys Val Thr Leu Thr Lys Lys Phe Phe Asp Lys Phe Thr Phe His
    50                  55                  60

Pro Asp Thr Leu Phe Leu Thr Gly Phe Val Ser Pro Thr Val Arg Leu
65                  70                  75                  80

Ser Thr Gln Ile Lys Pro Ile Leu Ser Ile Phe Arg Asn Lys Ile Phe
            85                  90                  95

Glu Ser Thr Leu Leu Val Asn Asn Asn Leu Asn Thr Asn Ala Gly Ala
            100                 105                 110

Ala Glu Ser Ser Ser Lys Lys Asn Val Val Val Glu Asn Ile Gln Met
        115                 120                 125

Gln Ile Thr Ser Gly Lys Glu Cys Arg Val Ile Phe Lys Phe Asn Cys
```

|     |     |     |     |     | 130 |     |     |     |     | 135 |     |     |     |     | 140 |     |
| --- | --- | --- | --- | --- | --- | --- | --- | --- | --- | --- | --- | --- | --- | --- | --- | --- |
| Lys 145 | His | Gly | Val | Val | Lys 150 | Thr | Tyr | Lys | Ile | Ala 155 | Tyr | Glu | Gln | Thr | Gln 160 |
| Thr | Leu | His | Ala | Val 165 | Phe | Asp | Lys | Ala | Ser 170 | Cys | His | Asn | Asn | Trp 175 | Gln |
| Ile | Asn | Ser | Lys 180 | Ile | Leu | Lys | Asp | Leu 185 | Ile | Glu | His | Phe | Gly 190 | Gln | Lys |
| Thr | Glu | Glu 195 | Leu | Thr | Ile | Gln | Pro 200 | Val | Gln | Gly | Arg | Val 205 | Leu | Leu | Thr |
| Ser | Phe 210 | Thr | Glu | Glu | Val | Val 215 | His | Asn | Lys | Asp | Val 220 | Leu | Lys | Gln | Pro |
| Thr 225 | Gln | Thr | Thr | Val | Ser 230 | Ile | Asp | Gly | Lys | Glu 235 | Phe | Glu | Gln | Val | Ser 240 |
| Leu | Asn | Glu | Gly | Ile 245 | Ile | Ile | Thr | Leu | Ser 250 | Leu | Lys | Glu | Phe | Arg 255 | Ala |
| Ala | Val | Leu | Leu 260 | Ala | Glu | Ser | Leu | Gly 265 | Thr | Ser | Ile | Ala | Ser 270 | Tyr | Tyr |
| Ser | Val | Ser 275 | Gly | Lys | Pro | Ala | Leu 280 | Phe | Thr | Phe | Asn | Lys 285 | Gly | Lys | Phe |
| Met | Glu 290 | Ile | Glu | Ala | Gln | Phe 295 | Ile | Leu | Ala | Thr | Val 300 | Met | Gly | Pro | Asp |
| Asp 305 | Phe | Asp | Glu | Ser | Ser 310 | Leu | Gly | Ala | Arg | Trp 315 | Gln | Gln | Ser | Gly | Thr 320 |
| Ala | Asn | Ser | Ser | Leu 325 | Leu | Val | Pro | Glu | Asn 330 | Thr | Ser | Ala | Ala | Pro 335 | Ala |
| Leu | Glu | Asn | Glu 340 | Ala | Pro | Ser | Ala | Ser 345 | Ile | Gly | Trp | Gln | Thr 350 | Asn | Gly |
| Asp | Ala | Glu 355 | Thr | Ser | Arg | Met | Phe 360 | His | Ser | Thr | Leu | Asp 365 | Ile | Pro | Arg |
| Asn | Glu 370 | Glu | Pro | Ala | Ala | Lys 375 | Pro | Ser | Arg | Gln | Thr 380 | Thr | Asp | Glu | Glu |
| Asn 385 | His | Pro | Leu | Phe | Leu 390 | Glu | Gly | Met | Pro | Asp 395 | Glu | Thr | Glu | Leu | Met 400 |
| Ala | Phe | Asp | Asn | Asp 405 | Val | Ala | Asp | Asp | Ala 410 | Glu | Phe | Gly | Pro | Thr 415 | Gln |
| His | Glu | Gln | Thr 420 | Tyr | His | Gly | Ile | Phe 425 | Ser | Gln | Asp | Asp | Thr 430 | Glu |     |
| Thr |     |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 426 amino acids
        ( B ) TYPE: amino acid
        ( C ) STRANDEDNESS: single
        ( D ) TOPOLOGY: linear ( i i ) MOLECULE TYPE: Amino Acid ( x i ) SEQUENCE DESCRIPTION: SEQ ID NO:3:

| Met 1 | Glu | Phe | Thr | Val 5 | Ser | Asn | Val | Asn | Leu 10 | Arg | Asp | Leu | Ala | Arg 15 | Ile |
| --- | --- | --- | --- | --- | --- | --- | --- | --- | --- | --- | --- | --- | --- | --- | --- |
| Phe | Thr | Asn | Leu 20 | Ser | Arg | Ile | Asp | Asp 25 | Ala | Val | Asn | Trp | Glu 30 | Ile | Asn |
| Lys | Asn | Gln | Ile 35 | Glu | Ile | Thr | Cys 40 | Leu | Asn | Ser | Ser | Arg 45 | Ser | Gly | Phe |

```
Ser  Met  Val  Thr  Leu  Lys  Lys  Ala  Phe  Phe  Asp  Lys  Tyr  Ile  Phe  Gln
     50                  55                      60

Pro  Asp  Ser  Val  Leu  Leu  Thr  Gly  Leu  Met  Thr  Pro  Thr  Ile  Arg  Ile
65                       70                  75                            80

Arg  Thr  Gln  Val  Lys  Pro  Ile  Leu  Ser  Val  Phe  Arg  Asn  Lys  Ile  Phe
                    85                       90                           95

Asp  Phe  Ile  Pro  Thr  Val  Val  Thr  Asn  Ser  Lys  Asn  Gly  Tyr  Gly
               100                      105                 110

Ser  Glu  Ser  Ala  Ser  Arg  Lys  Asp  Val  Ile  Val  Glu  Asn  Val  Gln  Ile
          115                      120                      125

Ser  Ile  Ser  Thr  Gly  Ser  Glu  Cys  Arg  Ile  Ile  Phe  Lys  Phe  Leu  Cys
     130                      135                      140

Lys  His  Gly  Val  Ile  Lys  Thr  Tyr  Lys  Ile  Ser  Tyr  Glu  Gln  Thr  Gln
145                      150                 155                          160

Thr  Leu  His  Ala  Val  Phe  Asp  Lys  Ser  Leu  Ser  His  Asn  Asn  Phe  Gln
                    165                      170                      175

Ile  Asn  Ser  Lys  Ile  Leu  Lys  Asp  Leu  Thr  Glu  His  Phe  Gly  Gln  Arg
               180                      185                      190

Thr  Glu  Glu  Leu  Thr  Ile  Gln  Pro  Leu  Gln  Glu  Arg  Val  Leu  Leu  Thr
          195                      200                 205

Ser  Phe  Thr  Glu  Glu  Val  Val  His  Asn  Arg  Asp  Ile  Leu  Lys  Gln  Pro
     210                      215                      220

Thr  Gln  Thr  Thr  Val  Ser  Ile  Asp  Gly  Lys  Glu  Phe  Glu  Arg  Val  Ala
225                      230                 235                          240

Leu  Asn  Glu  Gly  Val  Ser  Val  Thr  Leu  Ser  Leu  Arg  Glu  Phe  Arg  Ala
                    245                      250                      255

Ala  Val  Ile  Leu  Ala  Glu  Ala  Leu  Gly  Ser  Ser  Ile  Cys  Ala  Tyr  Tyr
               260                      265                      270

Gly  Val  Pro  Gly  Lys  Pro  Ile  Leu  Leu  Thr  Phe  Ala  Lys  Gly  Lys  Asn
          275                      280                 285

Ser  Glu  Ile  Glu  Ala  Gln  Phe  Ile  Leu  Ala  Thr  Val  Val  Gly  Ser  Asp
     290                      295                      300

Glu  Gln  Glu  Val  Ser  Ser  Met  Met  Gly  Asn  Arg  Trp  Gln  His  Ser  Ser
305                      310                      315                      320

Thr  Pro  Ala  Ser  Leu  Phe  Asn  Ser  Val  Glu  Arg  Asn  Asn  Ser  Leu  Thr
                    325                      330                      335

Ala  Val  Ala  His  Asn  Pro  Pro  Gly  Ser  Ile  Gly  Trp  Gln  Thr  Asp  Gln
               340                      345                 350

Ser  Asp  Ser  Ser  Arg  Met  Phe  Asn  Ser  Ala  Leu  Asp  Arg  Ser  Asp  Glu
          355                      360                 365

Thr  Asn  Gly  Ile  Lys  Glu  Pro  Ser  Thr  Thr  Asn  Asp  Ala  Gly  Gln  Ser
     370                      375                      380

Leu  Phe  Leu  Asp  Gly  Ile  Pro  Asn  Glu  Ser  Glu  Leu  Ala  Ala  Phe  Asn
385                      390                      395                      400

Asn  Asp  Val  Asn  Asp  Ala  Glu  Phe  Gly  Pro  Thr  Gln  Ala  Glu  Gln
                    405                      410                      415

Ser  Tyr  His  Gly  Ile  Phe  Ser  Gln  Glu  Asp
               420                      425
```

( 2 ) INFORMATION FOR SEQ ID NO:4:

( i ) SEQUENCE CHARACTERISTICS:
        ( A ) LENGTH: 171 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
CATGGTGACT   GAGATGTGCC   TTGGAGAGGA   GGATTTCCAG   CAGCTGCAGG   CCCAGGAAGG         60

GGTGGCCATC   ACTTTCTGCC   TCAAGGAATT   CCGGGGGCTC   CTGAGCTTTG   CAGAGTCAGC        120

AAACTTGAAT   CTTAGCATTC   ATTTTGATGC   TCCAGGCAGG   CCCGCCATCT   T                 171
```

( 2 ) INFORMATION FOR SEQ ID NO:5:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:5:

```
GCAGCTGCAG   GCCGAGGAAG   GGGTGGCCAT   CACTTTCTGC   CTCAAGGAAT   TCCGGGTGAG         60

GTTCCTCCCA   GGCGCTCGCC   GTCCTGTCCT   CCCTGCCCAG   CTCAGCCCAG   CCCGGGGCCT        120

CACCTGCACC   TCTTTCTCCA   GGGCTCCTGA   GCTTTGCAGA   GTCAGCAAAC   TTGAATCTTA        180

GCATTCATTT   TGATCCTCCA   GGCAGG                                                  206
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

```
CTGTTCTGCC   CTTCTCT                                                               17
```

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

```
TGCAGAGTCA   GCAAAC                                                                16
```

( 2 ) INFORMATION FOR SEQ ID NO:8:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

```
CCAATGACGA   CATTGA                                                                16
```

( 2 ) INFORMATION FOR SEQ ID NO:9:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:9:

CTTCCAGCAA TACCAG                                                                                    16

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

TGCATTGCAA CTTCGG                                                                                    16

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

AGGCTGAACC AAGAAC                                                                                    16

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

CGTTCCTACC TCTTAT                                                                                    16

( 2 ) INFORMATION FOR SEQ ID NO:13:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

GACAAGTTTT CCTTGC                                                                                    16

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:14:

TCAAGAGACC AGATGG 16

( 2 ) INFORMATION FOR SEQ ID NO:15:

(  i  ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:15:

GTTTGCTGAC TCTGCA 16

( 2 ) INFORMATION FOR SEQ ID NO:16:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:16:

AGAGAAGGGC AGAACAG 17

( 2 ) INFORMATION FOR SEQ ID NO:17:

(  i  ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:17:

CTGGTATTGC TGGAAG 16

( 2 ) INFORMATION FOR SEQ ID NO:18:

(  i  ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:18:

TCAATGTCGT CATTGG 16

( 2 ) INFORMATION FOR SEQ ID NO:19:

(  i  ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear (  i  i  ) MOLECULE TYPE: other nucleic acid (  x  i  ) SEQUENCE DESCRIPTION: SEQ ID NO:19:

GTTCTTGGTTC AGCCT 16

(2) INFORMATION FOR SEQ ID NO:20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CCATCTGGTC TCTTGA 16

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:21:

GCAAGGAAAA CTTGTC 16

(2) INFORMATION FOR SEQ ID NO:22:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:22:

ATAAGAGGTA GGAACG 16

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:23:

CATGGTGACT GAGATGTG 18

(2) INFORMATION FOR SEQ ID NO:24:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:24:

CCAAAAATCC TTGATGGTGA AGATGGCGGG CCTCCCTGGA GCATCAAAAT 50